United States Patent
Mendonsa et al.

(10) Patent No.: US 11,686,705 B2
(45) Date of Patent: Jun. 27, 2023

(54) GEL ELECTROPHORESIS FOR DNA PURIFICATION

(71) Applicant: Seagate Technology LLC, Fremont, CA (US)

(72) Inventors: Gemma Mendonsa, Minneapolis, MN (US); Tim Rausch, Farmington, MN (US); Riyan Alex Mendonsa, Minneapolis, MN (US)

(73) Assignee: SEAGATE TECHNOLOGY LLC, Fremont, CA (US)

( * ) Notice: Subject to any disclaimer, the term of this patent is extended or adjusted under 35 U.S.C. 154(b) by 344 days.

(21) Appl. No.: 16/870,580

(22) Filed: May 8, 2020

(65) Prior Publication Data

US 2021/0349054 A1  Nov. 11, 2021

(51) Int. Cl.
   G01N 27/447  (2006.01)
   C12N 15/10   (2006.01)

(52) U.S. Cl.
   CPC ..... *G01N 27/44791* (2013.01); *C12N 15/101* (2013.01); *G01N 27/4473* (2013.01)

(58) Field of Classification Search
   CPC ......... G01N 27/44791; G01N 27/4473; C12N 15/101
   See application file for complete search history.

(56) References Cited

U.S. PATENT DOCUMENTS

| | | | |
|---|---|---|---|
| 6,537,433 B1 * | 3/2003 | Bryning | C07K 1/26 204/600 |
| 7,179,357 B2 | 2/2007 | Lew et al. | |
| 7,381,317 B2 | 6/2008 | Liu et al. | |
| 7,435,545 B2 | 10/2008 | Liu et al. | |
| 9,728,387 B2 | 8/2017 | Mellors et al. | |
| 10,379,038 B2 | 8/2019 | Stavis et al. | |
| 2006/0254915 A1 | 11/2006 | Hirokawa et al. | |
| 2010/0084270 A1 * | 4/2010 | Vulto | C12N 15/101 204/461 |
| 2011/0062024 A1 * | 3/2011 | Sabin | G01N 27/44756 204/600 |

FOREIGN PATENT DOCUMENTS

WO   2009118420 A1   10/2009

OTHER PUBLICATIONS

D. R. Zalewski, et al., Electrokinetic sorting and collection of fractions for preparative capillary electrophoresis on a chip, Lab Chip, vol. 8, pp. 801-809, 2008 (Year: 2008).*
J. Chung, et al., Microfluidic packaging of high-density CMOS electrode array for lab-on-a-chip applications, Sensors and Actuators B, vol. 254, pp. 542-550 (2018) (Year: 2018).*

* cited by examiner

*Primary Examiner* — Maris R Kessel
(74) *Attorney, Agent, or Firm* — Holzer Patel Drennan

(57) ABSTRACT

Systems and methods for identifying DNA strand size and purifying the DNA based on strand size using electrophoresis. The methods include moving, via voltage, a plurality of DNA strands through a separation gel from an inlet of a capillary or passage to either a first outlet or a second outlet dependent on the DNA strand length. In some implementations, the system is a capillary electrophoresis system. In other implementations, the system is a microfluidic lab-on-a-chip.

13 Claims, 8 Drawing Sheets

GEL ELECTROPHORESIS FOR DNA PURIFICATION

BACKGROUND

Traditional gel electrophoresis used for DNA analysis and purification requires a large sample volume, several hours of preparation and run time, and several non-integrated instruments. Because of this, capillary electrophoresis is frequently used instead to analyze DNA. Capillary electrophoresis requires low volume samples, has run times that are only minutes long, and can be integrated into microfluidic chips for a single-instrument workflow. Currently, however, capillary electrophoresis is only used for analysis of DNA strand size. One desiring to purify DNA strands of a specific size from other strands in a solution is forced to use traditional gel electrophoresis.

SUMMARY

This disclosure is directed to systems and methods for identifying DNA strand size and purifying the DNA based on strand size using electrophoresis. The methods include moving, via voltage, a plurality of DNA strands through a separation gel from an inlet of a capillary or passage to either a first outlet or a second outlet dependent on the DNA strand length. Applied voltage to the outlets controls the path of the DNA strand.

One particular implementation described herein is an electrophoresis device having a fluid path having an inlet at a first end and a first outlet and a second outlet both at a second end, a separation gel within the fluid path, and a voltage source providing a voltage differential at the inlet, the first outlet and the second outlet, the voltage source configured to independently control the voltage differential at the first outlet and the second outlet in relation to the inlet. The electrophoresis device may be a capillary electrophoresis device, on a lab-on-a-chip platform with physically or non-physically bounded fluid path, or may be on an electrode-gridded lab-on-a-chip.

Another particular implementation described herein is n electrophoresis device having a structure having a main branch, a first branch off the main branch terminating at a first outlet and a second branch off the main branch terminating at a second outlet, a separation gel within the structure, and a voltage source providing a voltage differential at the inlet, the first outlet and the second outlet, the voltage source configured to independently control the voltage differential at the first outlet and the second outlet in relation to the inlet. The structure can be a capillary structure, or formed on a lab-on-a-chip.

Another particular implementation described herein is an electrophoresis system having a sample device and a control device. The sample device has a fluid path having an inlet at a first end and a first outlet and a second outlet both at a second end, a separation gel within the fluid path, and a voltage source providing a voltage differential at the inlet, the first outlet and the second outlet, the voltage source configured to independently control the voltage differential at the first outlet and the second outlet in relation to the inlet. The control device has a control fluid path having a control inlet at a first end and a control outlet at a second end, a separation gel within the control fluid path, and a control voltage source providing a voltage differential at the control inlet and the control outlet.

Another particular implementation described herein is a method of purifying a DNA sample using electrophoresis. The method includes providing a fluid path through a separation gel in an electrophoresis system having an inlet at a first end and a first outlet and a second outlet both at a second end, migrating a DNA sample from the first end through the fluid path to separate the DNA sample into separated DNA bands based on DNA strand length, responsive to applying a positive voltage proximate the first outlet, passing at least one separated DNA band through the first outlet, and responsive to applying a positive voltage proximate the second outlet, passing at least one different separated DNA band through the second outlet.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter. These and various other features and advantages will be apparent from a reading of the following detailed description.

BRIEF DESCRIPTION OF THE DRAWING

The described technology is best understood from the following Detailed Description describing various implementations read in connection with the accompanying drawing.

DETAILED DESCRIPTION

Figure 1:
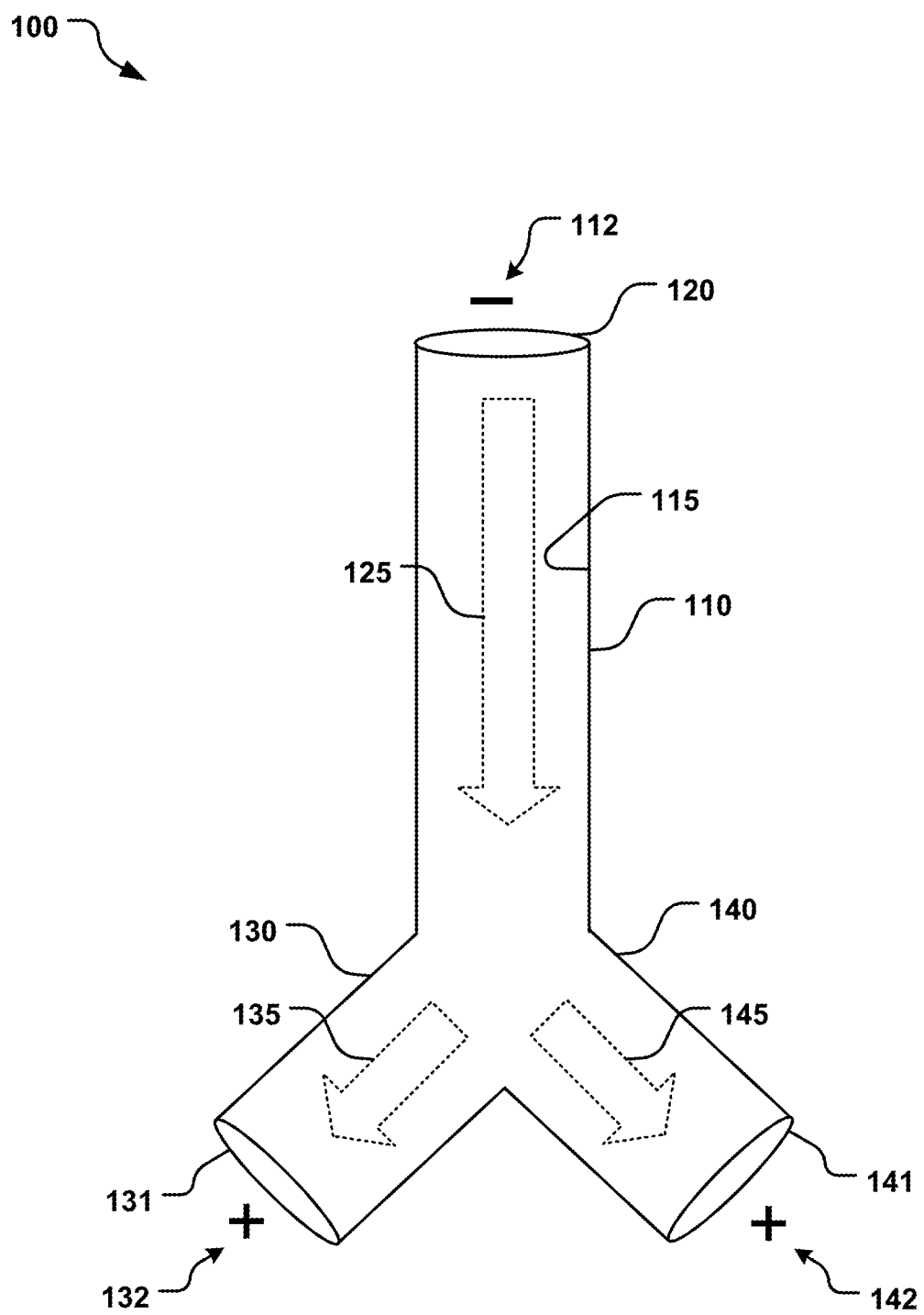
FIG. 1 is a schematic rendering of a capillary electrophoresis device of this disclosure with a control capillary electrophoresis system.

As indicated above, described herein is a type of capillary electrophoresis that can be used both for DNA analysis and for size-based DNA purification. Broadly, the capillary used for separation has an inlet at one end, a separation gel matrix in the capillary body, and two outlets branched from the main capillary body at the other end. The two outlets are used to separate the DNA strands by size, based on their travel speed through the separation gel. Control of the DNA strands through the two outlets is controlled by applied voltage at the outlets.

Software can be used to connect to the device and allow the user to specify the size of DNA to be collected. For example, the user may specify that the desired DNA strand length is 640 bp. The user may additionally or alternately specify a range of sizes to be collected: for example, the user may specify that all DNA strands in the size range of 600 bp to 700 bp be collected.

In the following description, reference is made to the accompanying drawing that forms a part hereof and in which is shown by way of illustration at least one specific implementation. The following description provides additional specific implementations. It is to be understood that other implementations are contemplated and may be made without departing from the scope or spirit of the present disclosure. The following detailed description, therefore, is not to be taken in a limiting sense. While the present disclosure is not so limited, an appreciation of various aspects of the disclosure will be gained through a discussion of the examples, including the figures, provided below. In some instances, a reference numeral may have an associated sub-label consisting of a lower-case letter to denote one of multiple similar components. When reference is made to a reference numeral without specification of a sub-label, the reference is intended to refer to all such multiple similar components.

Referring to FIG. 1, a generic capillary electrophoresis device 100 according to this disclosure is shown. The device 100 has a capillary structure 110 having a hollow interior 115 and an inlet 120 for receiving a DNA sample into the interior 115. The capillary structure may be a microfluidic channel, written gel line, gel coating, etc. The capillary structure 110 splits, divides, or separates into a first branch 130 and a second branch 140. In the particular structure shown, the capillary structure 110 is symmetrical, splitting into the first branch 130 and the second branch 140; the capillary structure 110 has a main branch that terminates where the first and second branches 130, 140 begin. In other implementations, the structure may not be symmetrical, but one branch may branch off before the other, or they may be different sizes (length, or width).

The first branch has a first outlet 131 from the interior 115 and the second branch 140 has a second outlet 141 from the interior. Present within the device 100 is a pathway 125 through the capillary structure 110, a first branch pathway 135 in the first branch 130 to the first outlet 131 and a second branch pathway 145 in the second branch 140 to the second outlet 141. In use, the capillary structure 110 has a separation gel matrix present in the interior 115, both in the main capillary structure 110 and the branches 130, 140. The separation gel matrix can be, for example, agarose, polyacrylamide, polyethylene glycol, or other suitable DNA electrophoresis compatible material.

As typical with capillary electrophoresis devices for DNA, the device 100 has a negative potential source (e.g., a negative electrode) 112 proximate the inlet 120, a positive potential source (e.g., a positive electrode) 132 proximate the first outlet 131 and another positive potential source (e.g., a positive electrode) 142 proximate the second outlet 141. A controller (not shown) can be used to turn on/off the potential sources (electrodes) 112, 132, 142.

Because DNA has an overall negative charge, a DNA strand moves through the separation gel matrix of the device 100 being pushed by the negative potential source 112 and pulled by the positive potential sources 132, 142 along the pathways 125, 135, 145. Which exit pathway 135 or 145 and thus outlet 131, 141 the DNA strand uses can be controlled by the positive potential sources 132, 142.

Figure 2:
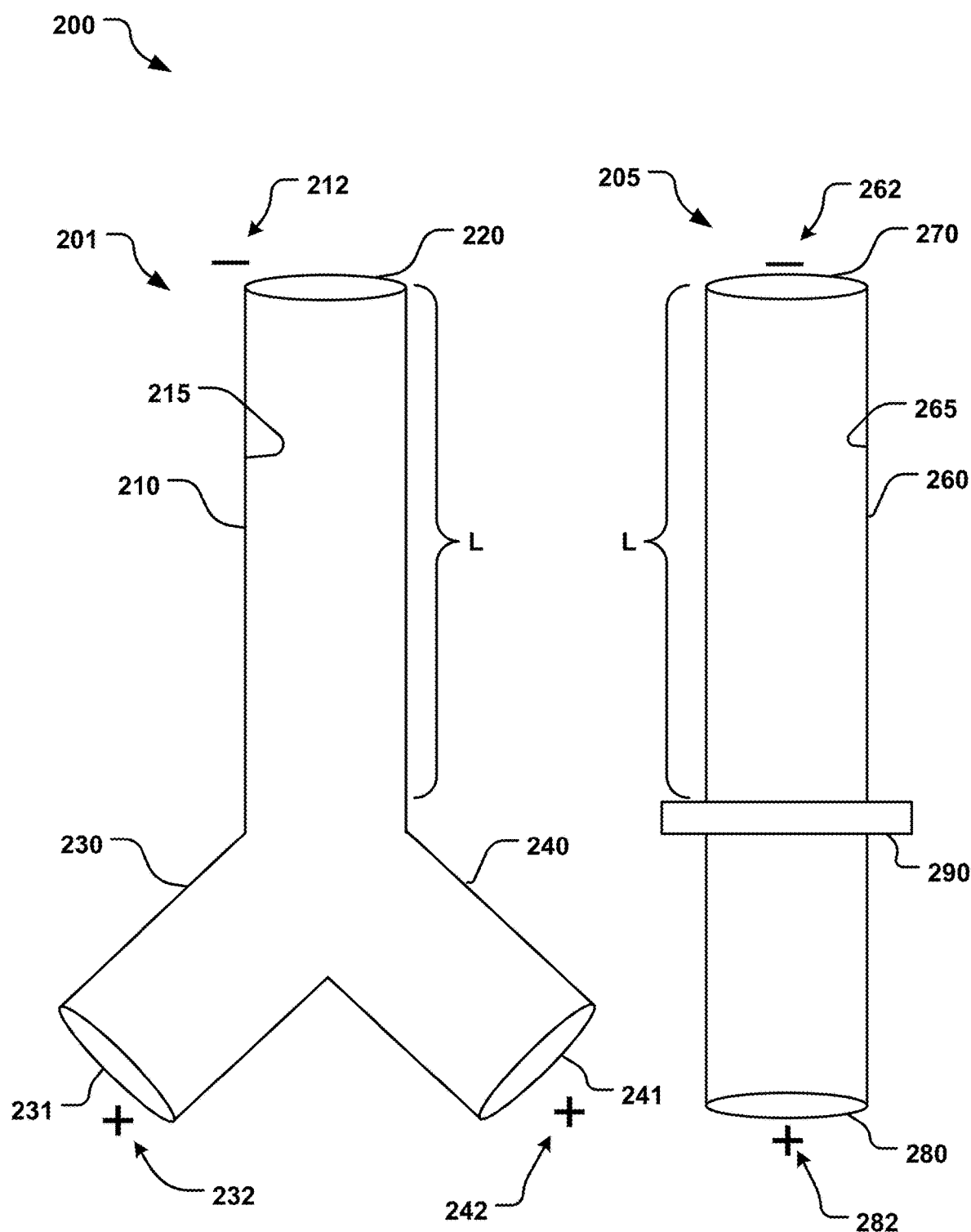
FIG. 2 is a schematic rendering of a capillary electrophoresis system having a capillary electrophoresis device of this disclosure and a control capillary electrophoresis device.

In FIG. 2, a capillary electrophoresis device, similar to that of FIG. 1, is shown as part of the system 200 that includes the device and a control capillary electrophoresis device. The system 200 includes a capillary electrophoresis device 201, similar to the device 100 of FIG. 1, having a capillary structure 210 having a hollow interior 215 and an inlet 220 into the interior 215 for receiving a DNA sample, a first branch 230 having a first outlet 231 from the interior 215 and a second outlet 240 from the interior 215. The device 200 has a negative potential source (e.g., a negative electrode) 212 proximate the inlet 220, a positive potential source (e.g., a positive electrode) 232 proximate the first outlet 231 and another positive potential source (e.g., a positive electrode) 242 proximate the second outlet 241. A controller (not shown) can be used to turn on/off the potential sources (electrodes) 212, 232, 242.

The system 200 also includes a control capillary electrophoresis device 205, also having a capillary structure 260 with a hollow interior 265, an inlet 270 into the interior 265 and an outlet 280 from the interior 265. The device 205 has a negative potential source 262 proximate the inlet 270 and a positive potential source 282 proximate the outlet 280. A controller (not shown) can be used to turn on/off the potential sources (electrodes), as desired. The control capillary electrophoresis device 205 also includes a detection window 290 to monitor (e.g., physically view) that portion of the interior 265.

Each device 201, 205 has a working length L of the capillary structure 210, 260 along which the DNA sample travels, which can be the same or essentially the same for the devices 201, 205. For the capillary electrophoresis device 201, the working length L is from the inlet 220 to no farther than the branch region; in some implementations, the working length L may terminate short of the branch region. For the control device 205, the working length L is from the inlet 270 to the detection window 290. In some implementations, the distance from the inlet 220 to the branch region is greater than the distance from the inlet 270 to the detection window 290. The detection window 290 in the control device 205 is upstream of where the branch occurs in the device 201.

The capillary electrophoresis device 100 of FIG. 1 and the capillary electrophoresis device 201 of FIG. 2 have the capillary tube structure 110, 210, respectively, that allow size identification of different sized DNA strands, and have the two branches 130, 140 and 230, 240, respectively, and outlets 131, 141 and 231, 241, respectively, that allow for physical separation (e.g., purification) of different sized DNA strands that are inputted into the devices 100, 201 via the inlets 120, 220. By using the devices 100, 201, a desired length or size of DNA strand can be collected via one outlet (e.g., 131, 231) while allowing the other lengths or sizes of DNA strands to go to the other outlet (e.g., 141, 241).

To use the system 200, a DNA ladder or size marker containing DNA strands of known, discrete sizes or lengths is loaded into the control device 205; the DNA marker sample can be labelled with a fluorescent or other marker dye. The size marker may be a commercially available DNA ladder, a customized mixture of DNA molecules of specific sizes, or a solution containing DNA molecules of a single specific size. The fluorescent dye may be an intercalating agent, such as ethidium bromide or SYBR green, or a covalently attached fluorescent tag.

In an alternate implementation, non-fluorescence based detection and collection methods may be used. For example, identification can be based on magnetic properties, electrical conductance, electrical resistance, Raman scattering, absorbance, chemiluminescence, etc.

An ionic buffer may be used to improve conduction of the applied voltage across the potential sources (electrodes). The buffer may be provided into the capillaries with the separation gel; in another implementation, the capillaries may be immersed in ionic buffer.

The DNA sample to be purified is loaded into the capillary device 201. In general, this DNA sample is not fluorescently or otherwise labelled, since the DNA collected will be used in downstream applications. However, a marker such as fluorescent dye may be added to the DNA sample to be purified as well as the DNA ladder to ensure precise synchronization of migration in both channels. In this case, downstream purification may be required to remove the marker.

A voltage differential is applied across the electrodes for each device 201, 205. DNA, which is negatively charged, will migrate through the separation gel matrix towards the positive electrode at the outlet. Smaller DNA strands will migrate more quickly through the gel matrix than larger strands. DNA strands of the same size tend to migrate together and appear as bands in the separation gel matrix.

As the size marker DNA migrates through the gel matrix, it passes a detection window in the control device. This window can be, e.g., a transparent window in the capillary device through which a laser, light, or other radiation of a specific wavelength shines. The radiation or other excitation source(s) may be a single fixed laser, multiple lasers, continuous laser, tunable laser, pulsed laser, LED, or lamp light source. The radiation excites the marked (e.g., fluorescent) molecules attached to the size marker DNA strand, resulting in the emission of photons. Emitted photons may be collected by lenses, gratings, or waveguides and, e.g., delivered to a photodetector. The software collects the information from the photodetector and uses it to track which size of band has just passed the detection window. Multiple detection windows may be present, e.g., to monitor the migration rate.

When the bands of DNA reach the detection window, the electrodes at the outlets can be activated/deactivated to control through which outlet the band exits the device. For example, one outlet can be termed a "collection" or "product collection" outlet and the other outlet can be termed "waste." When the desired sample DNA length is identified, it is directed towards the product collection outlet and is collected for downstream use. DNA strands longer and shorter than desired are directed towards the waste outlet. Referring to the example described above, if the desired DNA strand is 640 bp, the "product collection" electrode would turn on when the 600 bp marker passed the detection window and off when the 700 bp band passed the detection window.

A pump may be connected to the inlets and/or outlets to assist in moving the DNA samples into or out from the inlets and/or outlets.

Figure 3A:
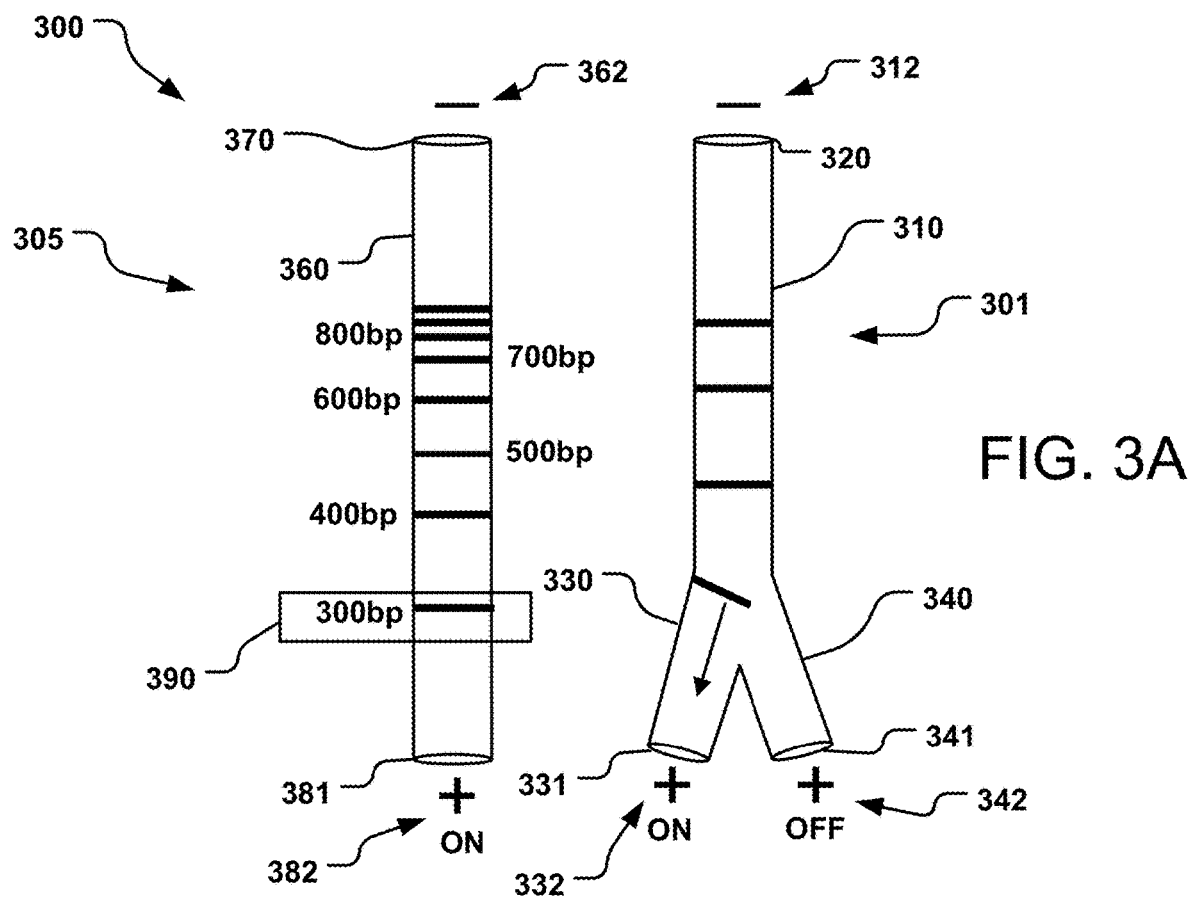
FIG. 3A and FIG. 3B are schematic rendering of the capillary electrophoresis system of FIG. 2 illustrating a DNA strand of a first length exiting the capillary system.
Figure 3B:
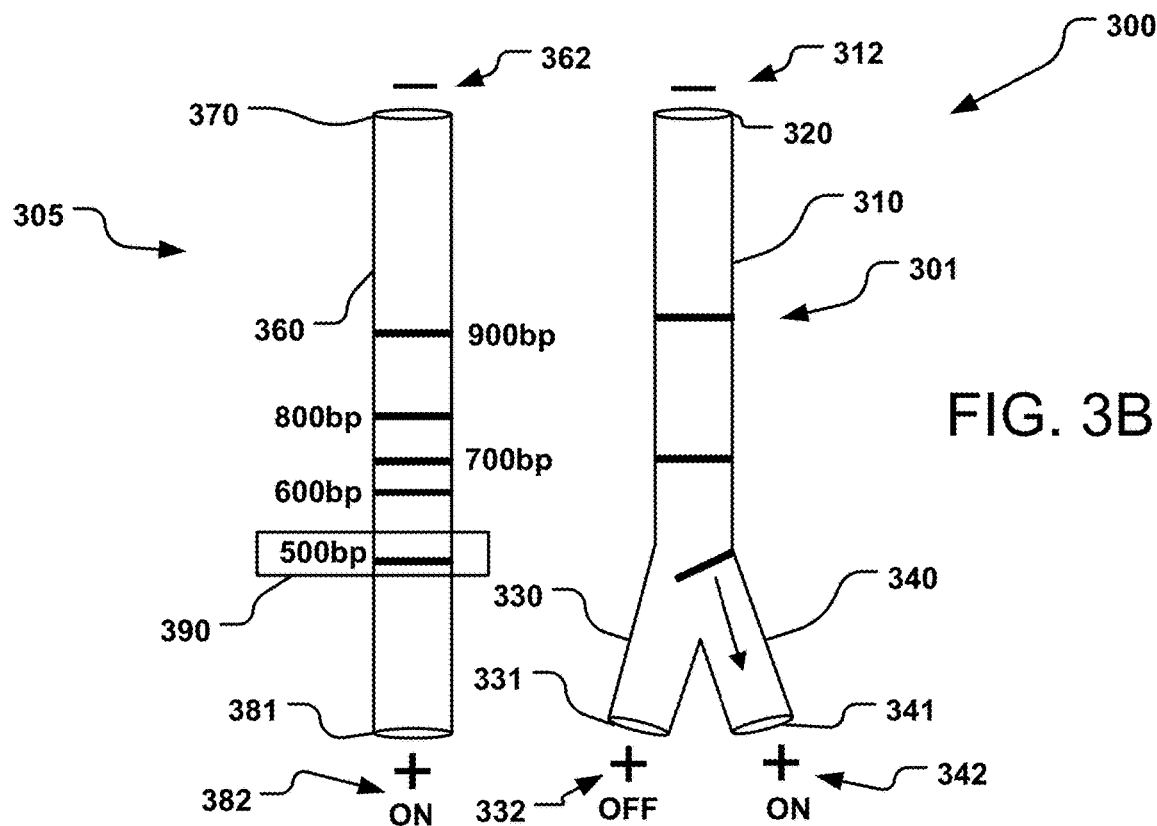

Turning to FIGS. 3A and 3B, use of the capillary electrophoresis device 100 or device 201 to separate a desired DNA strand length from a DNA sample having multiple DNA strands of different lengths is illustrated. FIGS. 3A and 3B illustrate a system 300 that includes a capillary electrophoresis device 301 and a control capillary electrophoresis device 305. Each of the devices 301, 305 are as described in FIG. 2.

The capillary electrophoresis device 301 has a capillary structure 310 having a hollow interior and an inlet 320 into the interior, a first branch 330 with a first outlet 331 from the interior and a second branch 340 with a second outlet 341 from the interior. The device 301 has a negative potential source (e.g., a negative electrode) 312 proximate the inlet 320, a positive potential source (e.g., a positive electrode) 332 proximate the first outlet 331 and another positive potential source (e.g., a positive electrode) 342 proximate the second outlet 341. A controller (not shown) can be used to turn on/off the potential sources (electrodes).

The control capillary electrophoresis device 305 also has a capillary structure 360 with a hollow interior, an inlet 370 into the interior and an outlet 380 from the interior. The device 305 has a negative potential source 362 proximate the inlet 370 and a positive potential source 382 proximate the outlet 380. The control device 305 includes a detection window 390.

Both the device 301 and the control device 305 have a separation gel matrix in the interior; such gels or matrixes are well known in the field of capillary electrophoresis.

A fluorescently dyed DNA size marker having multiple DNA strands of known different lengths is provided at the inlet 370 of the control device 305. Upon application of a voltage differential across the capillary structure 360, (e.g., applying negative potential via negative electrode 362 at the inlet 370 and/or applying positive potential via the positive electrode 382 at the outlet 380), the DNA strands are pulled and travel through the device 305 from the inlet 370 to the outlet 380. As well known in capillary electrophoresis, shorter DNA strands move through the separation gel matrix faster than longer DNA strands; thus, different length strands have a spacing therebetween along the length of the capillary structure 360. FIG. 3A shows various lengths of DNA strands (e.g., 300 bp, 400 bp, 500 bp, 600 bp, etc.) longitudinally separating in the capillary tube 360, with DNA strands having 300 bp length shown in the detection window 390. The strands are readily detectable because of the fluorescent dye, e.g., by laser, light, or other radiation of a specific wavelength (e.g., visible, IR, near IR, UV, etc.).

To separate and purify a DNA sample having multiple, unknown, lengths of strands using the system 300, the DNA sample is started in the device 301 at the inlet 320 at the same time or soon after the DNA size marker is started at the inlet 370 in the control device 305. Upon application of a voltage differential across the capillary structure 310, (e.g., applying negative potential via negative electrode 312 at the inlet 320 and/or applying positive potential via one or both of the positive electrodes 332, 342 at the outlets 330, 340), the DNA strands travel through the device 301 from the inlet 320 towards the outlets 330, 340. The shorter DNA strands move through the separation gel matrix faster than longer DNA strands; thus, different length strands have a spacing therebetween along the length of the capillary structure 310. The various lengths of DNA strands longitudinally separate in the capillary tube 310 due to their different lengths.

Strands of same length move through the separation gel and the devices 301, 305 at the same (or essentially the same) rate. Due to the detection window 390 in the control device 305, the approximate speed of the various strand lengths is known. Because the DNA sample in the device 301 was started at the same time or soon (e.g., within a fraction of a second) after the control sample in the control device 305, the same or similar length strand is at approximately the same location in the device 301 as in the control device 305.

As seen in FIG. 3A, DNA strands of about 300 bp are detected in the detection window 390; the same or similar length DNA strands are thus in approximately the same location in the device 301, having traveled through the separation gel at or essentially at the same speed. By knowing the length of the strand approaching the branch, different lengths of DNA strands can be separated and purified.

In FIG. 3A, the electrode 332 at the first inlet 331 is shown "on" and the electrode 342 at the second outlet 341 is "off." The positive charge from the electrode 332 thus pulls the DNA strand through the branch 330 and to the outlet 331.

Subsequently, as seen in FIG. 3B, DNA strands of about 500 bp are detected in the detection window 390; the same or similar length DNA strands are thus in approximately the same location in the device 301, having traveled through the separation gel at or essentially at the same speed. The electrode 332 at the first inlet 331 is shown "off" and the electrode 342 at the second outlet 341 is "on," thus pulling the DNA strand through the branch 340 and to the outlet 341.

In such a manner, the desired DNA strand lengths can be collected at one outlet versus the other.

A challenge that might be encountered is a difference in DNA migration rate through the separation gel between the capillary device and the control device. To address this issue, the system may be calibrated to correct for differences in migration rate. To calibrate the capillary device migration rate to the control capillary device migration rate, a fluorescently or otherwise labelled DNA sample of a uniform, small size (e.g., 150 bp) is added to both capillary devices. A calibration band detection window is located upstream of the detection window, close to the inlets. The time that the calibration band reaches the calibration band detection window is recorded for both devices. If the times are not the same, the software can add a delay between the band detection and the electrode switching times.

Figure 4:
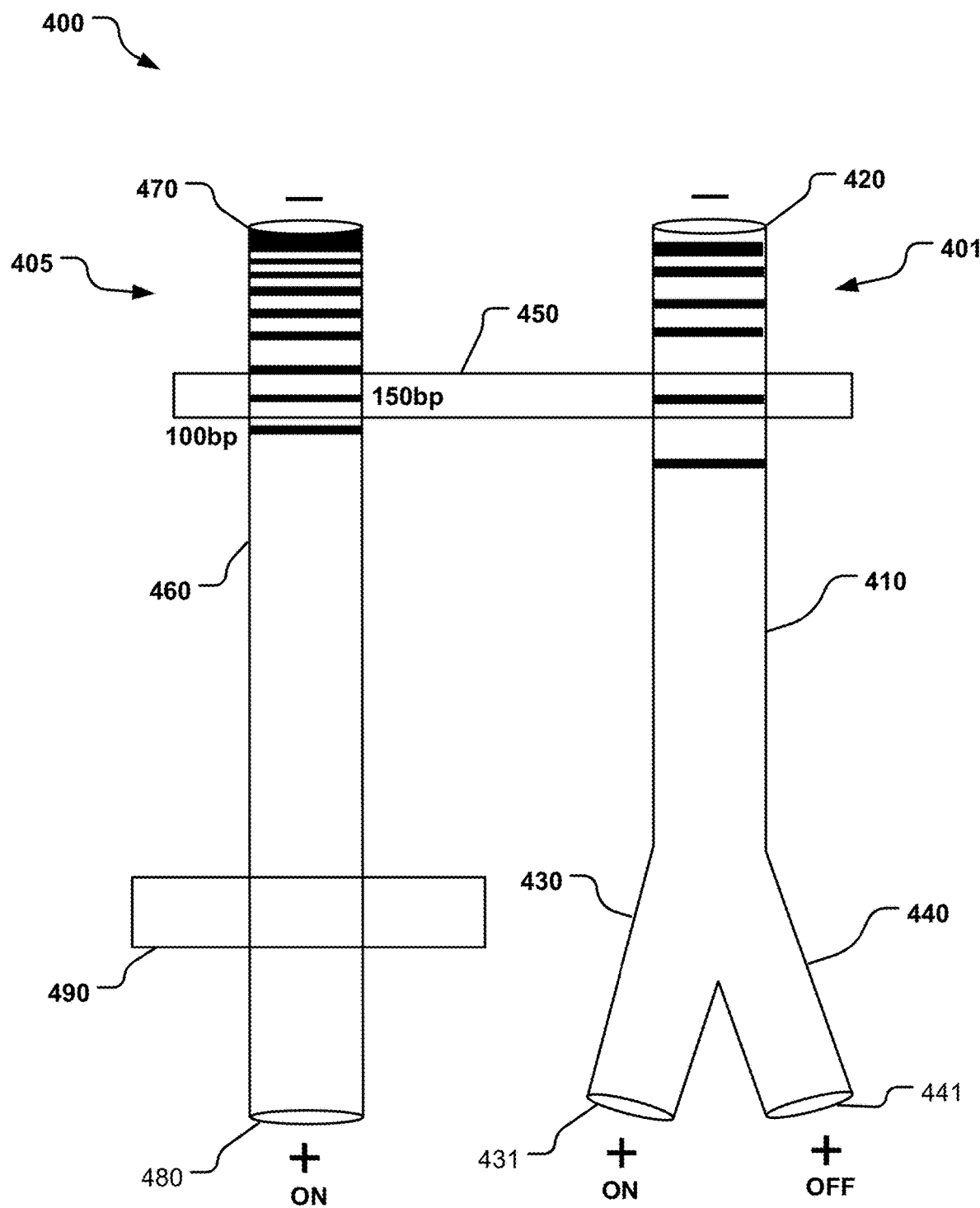
FIG. 4 is a schematic rendering of a calibration method for the capillary electrophoresis system of FIG. 2.

FIG. 4 illustrates a calibration method that can be used to correct for asynchronous DNA travel rates. A system 400 includes a capillary electrophoresis device 401 and a control capillary electrophoresis device 405. Each of the devices 401, 405 are as described in FIG. 2 and FIGS. 3A, 3B and the details are not repeated here.

The capillary electrophoresis device 401 has a capillary structure 410 with an inlet 420, a first branch 430 with a first outlet 431 and a second branch 440 with a second outlet 441. The device 401 has a negative potential source proximate the inlet 420, a positive potential source proximate the first outlet 431 and another positive potential source proximate the second outlet 441. The control capillary electrophoresis device 405 also has a capillary structure 460 with an inlet 470 and an outlet 480. The device 405 has a negative potential source proximate the inlet 470 and a positive potential source proximate the outlet 480. The device 405 also has a detection window 490. Both the device 401 and the control device 405 have a separation gel matrix in the interior of the capillary structure. Additionally, both the device 401 and the control device 405 have a calibration detection window 450, that in this schematic diagram, extends across both capillary structures 410, 460. In some implementations, several calibration band detection windows may be present, to account for any propagation of rate de-synchronization as the DNA migrates through the gel matrix.

A fluorescently dyed DNA size marker having a specific length DNA strand is provided to both devices 401, 405, at the inlet 420 of the device 401 and at the inlet 470 of the control device 405. The specific DNA strand length is detected by the calibration detection window 450 as they pass. If the bands in the two devices 401, 405 do not pass the calibration window 450 at the same time, an offset or delay between the two devices 401, 405 is established. Future separation runs using the devices can be done subsequent to calibration of the devices 401, 405 based on the detected offset or delay.

To further enhance the calibration technique, several detection windows may be present in series in the device. For example, a system or device may have three narrow detection windows in series. If the DNA is migrating through both devices evenly at the same time, as the marker band of interest passed the middle detection window, the outlet electrodes would switch. If the DNA is migrating faster through the sample capillary device than the control device, the electrodes would switch as the marker band of interest passed the last detection window. If the DNA is migrating faster through the control capillary device than the sample capillary device, the electrodes would switch as the marker band of interest passed the first detection window.

Figure 5:
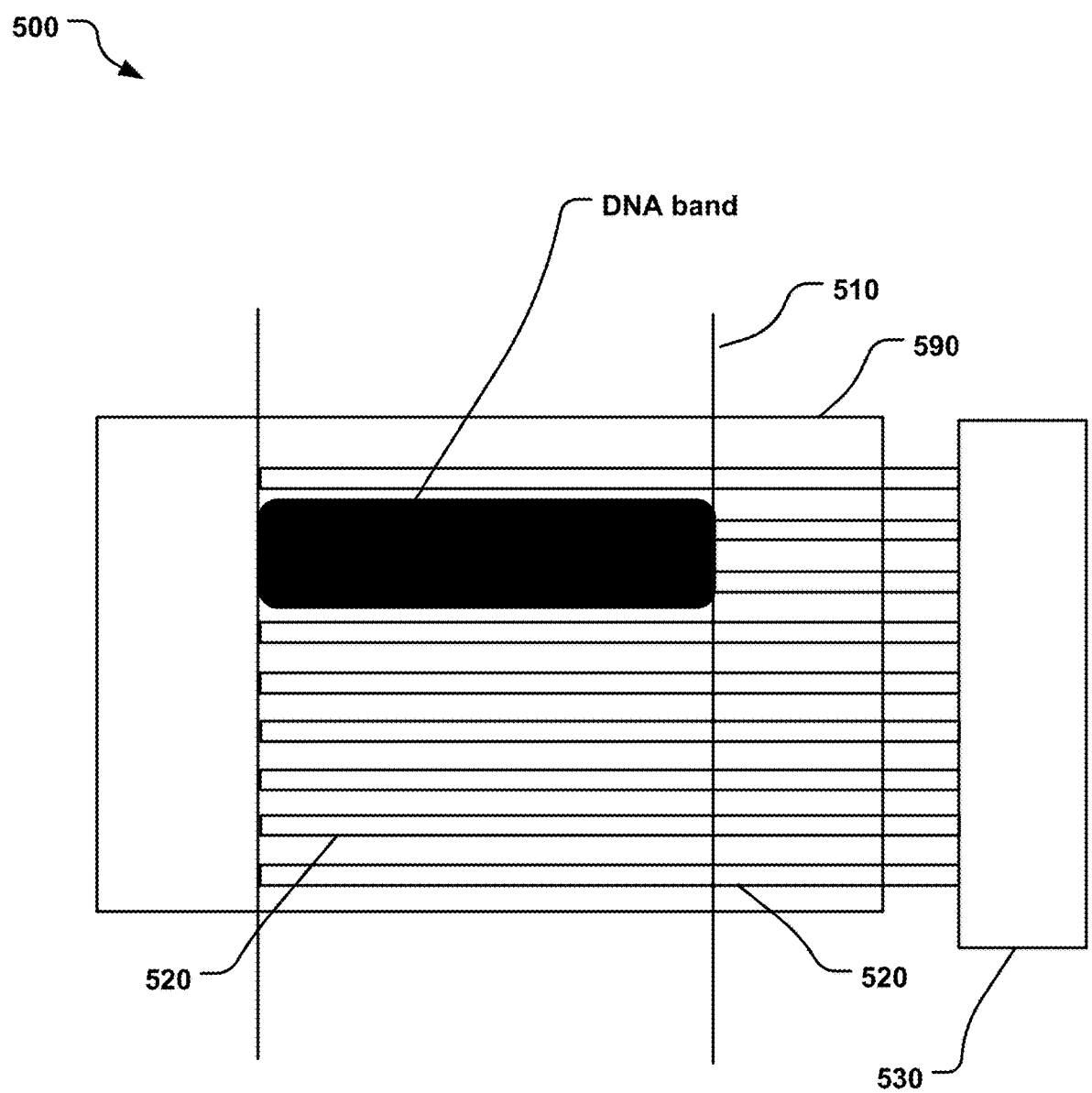
FIG. 5 is an enlarged schematic diagram of a portion of a capillary electrophoresis device.

Alternatively, rather than several detection windows in series, a single wide detection window may be used, e.g., interfaced with a series of waveguides coupled to a photodiode array. Fluorescent emitted light is collected by the waveguides as the marked sample passes over them and is delivered to the photodiode array, giving precise positional information. FIG. 5 illustrates an enlarged view of such a device.

In FIG. 5, the device 500 has a detection window 590. A plurality of waveguides 520 extending in the detection window 590 are each coupled to a photodiode present in a photodiode array 530. The waveguides 520 collect light (e.g., fluorescent) from DNA strands as they pass through the detection window 590. The precise position of the DNA strands in the detection window 590 can be determined based on which photodiodes in the array 530 receive the signal from the waveguides 520.

It is noted that any of the detection windows and calibration band detection windows can be interfaced with light collection and/or light detection systems. Light may be indirectly detected at the detection window by a photodiode array as in FIG. 5, or directly at the detection window by a photodiode array. Light may be collected and focused by mirrors, lenses, or waveguides perpendicular to or parallel to the light source. Collected light may be filtered, e.g., such that only photons of specific wavelengths are detected. Any light filtration may be performed with any number of ring resonators, waveguides (as in FIG. 5), diffraction gratings, prisms, edge filters, notch filters, bandpass filters, directional couplers, MZI (Mach-Zehnder Interferometer) filters, AWG (array waveguide gratings), etc.

The collected light can be delivered to the detection system for detection and/or quantification by, e.g., a photomultiplier tube, photodiode array, charge-coupled device, electron multiplied charge-coupled device, etc.

The previous devices and systems have utilized capillary devices having submillimeter diameter, elongate, hollow structures.

The electrophoresis devices and systems can alternately be provided as microfluidic or nanofluidic systems. One particular microfluidic system is a microfluidic lab-on-a-chip system; two alternative microfluidic lab-on-a-chip systems are provided below.

Lab-on-a-chip is a common term for an integrated circuit ("chip") on which one or several laboratory functions or chemical reactions are done. The chip can be no more than a few square centimeters. Labs-on-a-chip handle extremely small fluid volumes (e.g., measured as e.g., microliters, nanoliters, or pico-liters) and are often called microfluidic systems. In digital microfluidics, the lab-on-a-chip has a hydrophobic "chip platform" on which fluid droplets (e.g., liquid droplets) can be manipulated by precisely controlled voltage application.

The chip may be formed from two or more detachable parts: one part containing electronics, waveguides and photodetectors, another part containing the capillaries and gel, and another part containing sample inlets and interfaces to other microfluidic channels or liquid lines. Such a construction would enable the reuse of expensive electronic and photonic pieces and the disposable of the fluidic area. The platform may have a cover plate covering the fluidic area. By utilizing the feature of surface tension of the fluid on the platform, the fluid can be precisely moved across the platform by voltage applied to the platform, e.g., in a grid.

Figure 6:
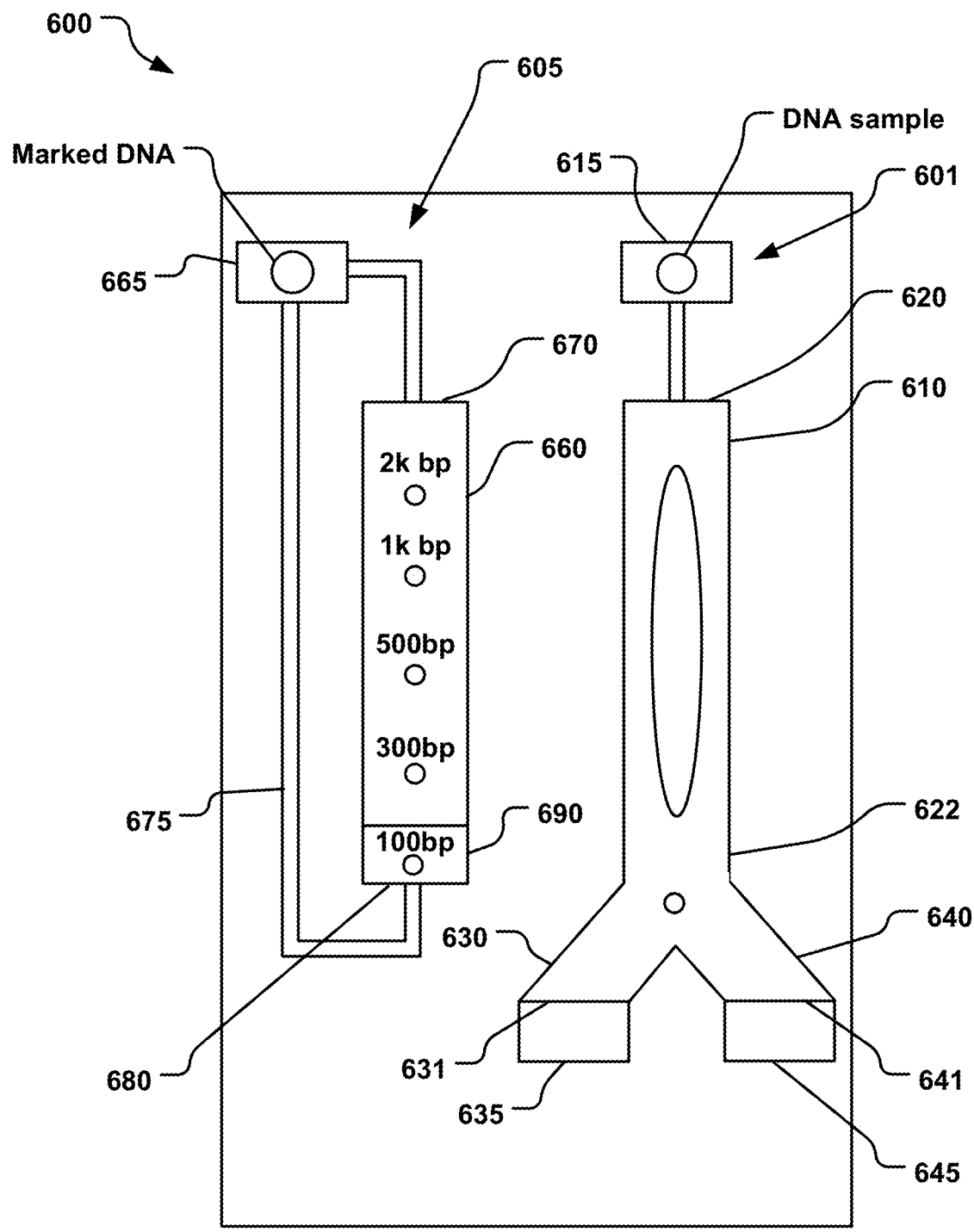
FIG. 6 is a schematic diagram of an electrophoresis system formed as a lab-on-a-chip.
Figure 7:
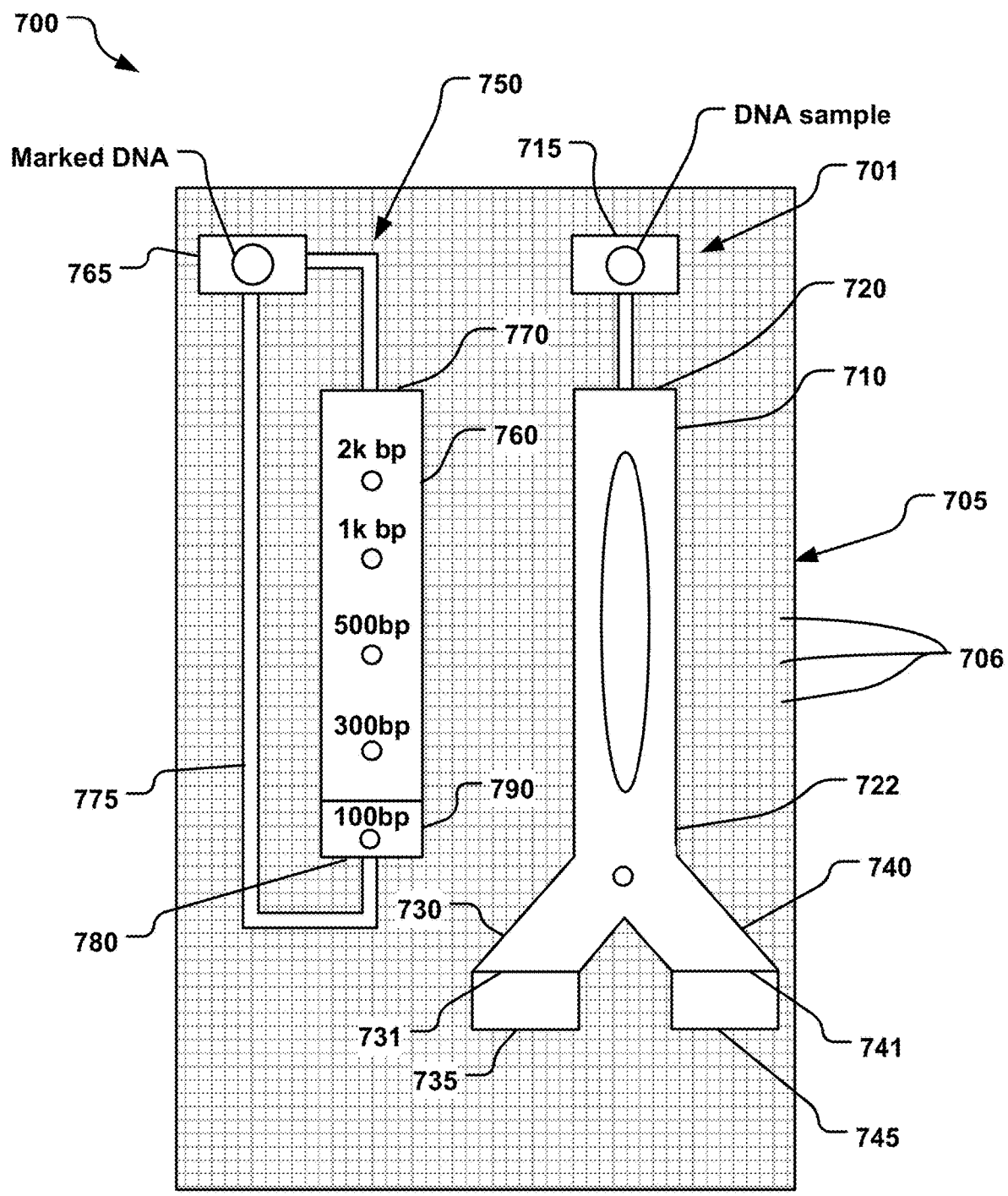
FIG. 7 is a schematic diagram of another electrophoresis system formed as a lab-on-a-chip.
Figure 8:
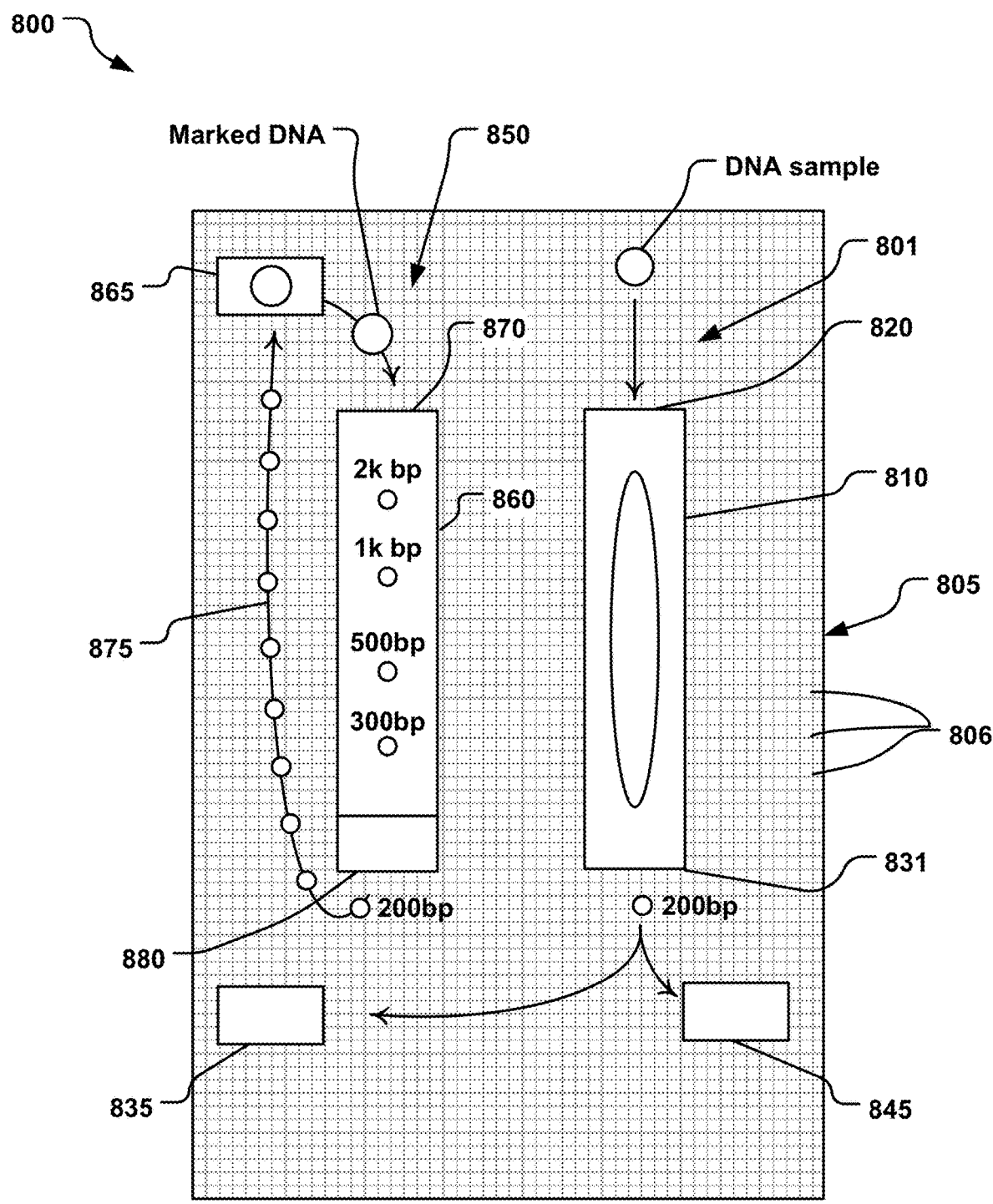
FIG. 8 is a schematic diagram of another electrophoresis system formed as a lab-on-a-chip.

FIGS. 6, 7 and 8 shows implementations of electrophoresis systems implemented on a lab-on-a-chip or microfluidic platform.

FIG. 6 shows a microfluidic system 600, having a platform working surface, also referred to as a lab-on-a-chip. In this implementation, the platform working surface has an insulating layer (e.g., silicon, silicon dioxide, etc.) over the working surface and a plurality of channels present through the insulating layer to the working surface. The plurality of channels, through the insulating layer to the working surface, physically define the electrophoresis devices of the system. The strands in the DNA sample and the marked DNA sample are moved through the channels on the chip using a pressure source (e.g., pump, blister package, etc.) connected to the inlets and/or the outlets.

The system 600 includes an electrophoresis device 601 having a main channel 610 with an inlet 620 for receiving a DNA sample, a first branch 630 having a first outlet 631 and a second branch 640 having a second outlet 641. The main channel structure 610, first branch 630 and second branch 640 have a separation gel matrix therein. The device 601 includes holding well 615 fluidically connected to the inlet 620, a first receiving well 635 fluidically connected to the first outlet 631 and a second receiving well 645 fluidically connected to the second outlet 645. By application of a positive pressure to the inlet 620 and/or a negative pressure at the outlets 631, 641 at the appropriate time, a DNA sample can be moved through the device 601, from the holding well 615 through the main channel 610 and along either the first branch 630 or the second branch 640. Because the main channel 610, the holding well 615 and the branches 630, 640 are channels in the insulating layer on the working surface of the platform, the movement of the DNA sample is limited to these features.

The system 600 also includes a control electrophoresis device 605, also having a main channel 660 with an inlet 670 for receiving a marked DNA sample, an outlet 680, and an appropriate pressure source(s) to move the marked DNA through the device 605. Separation gel matrix is present in the main channel 660. The control electrophoresis device 605 also includes a detection window 690. The device 605 also includes holding well 665 fluidically connected to the inlet 670. By application of a positive pressure to the inlet 670 and/or a negative pressure at the outlet 680 at the appropriate time, the marked DNA sample can be moved through the device 605, from the holding well 665 through the main channel 660 to the outlet 680. In this implementation, an optional recycle channel 675 extends from the outlet 680 to the holding well 665, allowing reuse of the marked DNA sample. Because the main channel 660, the holding well 665 and the recycle channel 675 are channels in the insulating layer on the working surface of the platform, the movement of the marked DNA sample is limited to these features.

In some implementations, another holding well may be present between the outlet 680 and holding well 665 in the recycle channel 675, to allow all strand lengths of the DNA sample to come together before being recycled and reused.

Similar to the capillary electrophoresis devices and systems described above, the system 600 allows size identification of different sized DNA strands and physical separation (e.g., purification) of different sized DNA strands. By using the system 600 and the devices 601, 605, a desired length or size of DNA strand can be collected via one outlet (e.g., 631) while allowing the other lengths or sizes of DNA strands to go to the other outlet (e.g., 641).

To use the system 600, a DNA size marker containing DNA strands of known, discrete sizes or lengths is loaded into the holding well 665 of the control device 605; the DNA marker sample can be labelled with a fluorescent or other marker dye. The DNA sample to be purified is loaded into the holding well 615 of the device 601. In general, this DNA sample is not fluorescently or otherwise labelled, since the DNA collected will be used in downstream applications. Buffer may be added to the holding wells 615, 665 to dilute the DNA samples.

Appropriate pressure is applied to move the control DNA sample from the holding well 665 to the inlet 670; similarly, appropriate pressure is applied to move the DNA sample from the holding well 615 to the inlet 620. A negative charge at the inlets 620, 670 pushes the DNA strands from the inlets 620, 670 through the separation gel matrix to the outlets 631, 641, 680, and/or a positive charge at the outlets 631, 641, 680 pulls the DNA strands from the inlets 620, 670 to the outlets 631, 641, 680. As explained above, smaller DNA strands migrate more quickly through the gel matrix than larger strands; various lengths of DNA strands (e.g., 100 bp, 300 bp, 500 bp, 1000 bp, etc.) are seen longitudinally separated in the device 605, with DNA strands having 100 bp length shown in the detection window 690.

When the marked bands of DNA reach the detection window 690, the approximate location of the same band in the DNA sample are known, and the electrodes can be activated/deactivated to control through which branch 630, 640 and outlet 631, 641 the desired band exits the device 601. As before, one outlet and receiving well can be termed a "collection" or "product collection" and the other outlet and receiving well can be termed "waste." When the desired sample DNA length is identified in the detection window 690, it is directed towards the product collection outlet and is collected in the receiving well for downstream use. DNA strands longer and shorter than desired are directed towards the waste outlet and receiving well.

DNA strands exiting the control device 605 via the outlet 680 can be reused for a subsequent run. From the outlet 680, the DNA can be moved through the recycle channel 675 back to the holding well 665. Buffer may be added to the holding well 665 to rehydrate or dilute the marked DNA sample.

FIG. 7 shows another microfluidic system having channels formed in a substrate to limit the path of the DNA samples. The system 700 in FIG. 7 has an electrode-gridded platform working surface 705 having numerous cells 706, at least some of which are configured to independently receive a voltage. In this implementation, the platform working surface 705 has an insulating layer (e.g., silicon, silicon dioxide, etc.) over the working surface and a plurality of channels present through the insulating layer to the working surface. The plurality of channels, through the insulating layer to the working surface, physically define the electrophoresis devices of the system. Using known techniques (e.g., voltage differential on the platform), the strands in the DNA sample and the marked DNA sample are moved through the channels on the chip to the appropriate device and the separation gel matrix where separation of the DNA strands occurs.

Similar to the previous system, the system 700 includes an electrophoresis device 701 having a main channel 710 with an inlet 720 for receiving a DNA sample, a first branch 730 having a first outlet 731 and a second branch 740 having a second outlet 741. The main channel structure 710, first branch 730 and second branch 740 have a separation gel matrix therein. The device 701 includes holding well 715 fluidically connected to the inlet 720, a first receiving well 735 fluidically connected to the first outlet 731 and a second receiving well 745 fluidically connected to the second outlet 745. By application of voltage to the cell(s) 706 proximate the inlets 720 and/or the outlets 731, 741 at the appropriate time, a DNA sample can be moved through the device 701, from the holding well 715 through the main channel 710 and along either the first branch 730 or the second branch 740. Because the main channel 710, the holding well 715 and the branches 730, 740 are channels in the insulating layer on the working surface of the platform, the movement of the DNA sample is limited to these features.

The system 700 also includes a control electrophoresis device 750, also having a main channel 760 with an inlet 770 for receiving a marked. DNA sample and an outlet 780. Separation gel matrix is present in the main channel 760. The control electrophoresis device 750 also includes a detection window 790. The device 750 also includes holding well 765 fluidically connected to the inlet 770. In this implementation, an optional recycle channel 775 extends from the outlet 780 to the holding well 765, Because the main channel 760, the holding well 765 and the recycle channel 775 are channels in the insulating layer on the working surface of the platform, the movement of the DNA sample is limited to these features.

In some implementations, another holding well may be present between the outlet 680 and the recycle channel 675, to allow all strands lengths of the DNA sample to come together before being recycled.

Similar to the capillary electrophoresis devices and systems described above, the system 700 allows size identification of different sized DNA strands and physical separation (e.g., purification) of different sized DNA strands. By using the system 700 and the devices 701, 750, a desired length or size of DNA strand can be collected via one outlet (e.g., 731) while allowing the other lengths or sizes of DNA strands to go to the other outlet (e.g., 741).

To use the system 700, a DNA size marker containing DNA strands of known, discrete sizes or lengths is loaded into the holding well 765 of the control device 750; the DNA marker sample can be labelled with a fluorescent or other marker dye. The DNA sample to be purified is loaded into the holding well 715 of the device 701. Buffer may be added to the holding wells 715, 765 to dilute the DNA samples.

Appropriate cells 706 on the platform receive a voltage to move the control DNA sample from the holding well 765 to the inlet 770; similarly, appropriate cells 706 on the platform receive a voltage to move the DNA sample from the holding well 715 to the inlet 720.

A negative voltage is applied proximate the inlets 720, 770 and/or a positive voltage is applied at the outlets 731, 741, 780, to pull the DNA strands from the inlets 720, 770 through the separation gel matrix to the outlets 731, 741, 780. As explained above, smaller DNA strands migrate more quickly through the gel matrix than larger strands; various lengths of DNA strands (e.g., 100 bp, 300 bp, 500 bp, 1000 bp, etc.) are seen longitudinally separated in the device 750, with DNA strands having 100 bp length shown in the detection window 790.

When the marked bands of DNA reach the detection window 790, the approximate location of the same band in the DNA sample are known, and the cells 706 on the platform proximate the outlets 731, 741 can be activated/deactivated to control through which branch 730, 740 and outlet 731, 741 the desired band exits the device 701. As before, one outlet and receiving well can be termed a "collection" or "product collection" and the other outlet and receiving well can be termed "waste." When the desired sample DNA length is identified in the detection window 790, it is directed towards the product collection outlet and is collected in the receiving well for downstream use. DNA strands longer and shorter than desired are directed towards the waste outlet and receiving well.

DNA strands exiting the control device 750 via the outlet 780 can be reused for a subsequent run. From the outlet 780, the DNA can be moved through the recycle channel 775 back to the holding well 765. Buffer may be added to the holding well 765 to rehydrate or dilute the marked DNA sample.

FIG. 8 also shows a microfluidic system having an electrode-gridded platform working surface 805 having numerous cells 806 each configured to independently, receive a voltage. In this implementation however, the cells 806 of the platform control the movement of the DNA thereon by the applied voltage, rather than physical channels. Using known techniques (e.g., voltage differential on the platform), the strands in the DNA sample and the marked DNA sample are moved on (across) the platform to the device and the separation gel matrix where separation of the DNA strands occurs.

Similar to the previous implementations, the microfluidic system 800 includes an electrophoresis device 801 having a main region 810 where a separation gel matrix is present. The main region 810 has an inlet 820 for receiving a DNA sample and an outlet 830. Also present on the microfluidic platform is a first receiving well 835 and a second receiving well 845; these wells 835, 845 may be physical structures or may merely be an area on the platform. By application of voltage to the individual cells 806 on the platform at the appropriate time, a DNA sample can be moved through to the inlet 820 of the device 801 and through the main region 810. At the outlet 830, the design DNA strands can be moved to either the first receiving well 835 or the second receiving well 845 by applying voltage to the appropriate cells 806.

The system 800 also includes a control electrophoresis device 850, also having a main region 860 with an inlet 870 for receiving a marked DNA sample and an outlet 880. The control electrophoresis device 850 also includes a detection window 890. The device 850 can include holding well 865 to store the marked DNA sample when not being run in the device.

Similar to the electrophoresis devices and systems described above, the system 700 allows size identification of different sized DNA strands and physical separation (e.g., purification) of different sized DNA strands.

To use the system 800, a DNA size marker containing DNA strands of known, discrete sizes or lengths can provided into the holding well 865 of the control device 850 or merely on the microfluidic platform of the device 850; the DNA marker sample can be labelled with a fluorescent or other marker dye. The DNA sample to be purified is provided on the microfluidic platform of the device 801. Appropriate cells 806 on the platform receive a voltage to move the marked DNA sample to the inlet 870; similarly, appropriate cells 806 on the platform receive a voltage to move the DNA sample to the inlet 820.

A negative voltage is applied to the inlets 820, 870 and/or a positive voltage is applied at the outlets 830, 880, to pull the DNA strands from the inlets 820, 870 through the separation gel matrix to the outlets 730, 780. If desired, by application of voltage to the individual cells 806 on the platform at the appropriate time, a DNA sample can be moved through the devices 801, 850. As explained above, smaller DNA strands migrate more quickly through the gel matrix than larger strands; various lengths of DNA strands (e.g., 200 bp, 300 bp, 500 bp, 1000 bp, etc.) are seen longitudinally separated in the device 750, with DNA strands having 200 bp length shown already through the detection window 790 and past the outlet 780.

Because the location of the marked 200 bp band of DNA is known, the approximate location of the same band in the DNA sample is known. The cells on the platform at the outlet 831 can be activated/deactivated to control where the band is collected, either the first receiving well 835 or the second receiving well 845.

Marked DNA strands exiting the control device can be reused for a subsequent run. From the outlet 880, the DNA can be moved through a recycle path 875 back to the holding well 865.

The devices and systems described herein enable users to purify small amounts of DNA based on strand size or length. Capillary electrophoresis requires only minutes of preparation and run time as opposed to hours in traditional gel electrophoresis. The devices and systems described herein require minimal user input and eliminate the use of several different instruments to run and image the gel and eliminate the need for a user to physically excise the band of interest from the gel. The microfluidic chip system can be inexpensive, particularly if disposable capillary devices are interfaced with photonic and electronic components. The devices and systems described herein provide a faster and easier way to purify DNA based on size than currently available methods.

The above specification and examples provide a complete description of the structure and use of exemplary implementations of the invention. The above description provides specific implementations. It is to be understood that other implementations are contemplated and may be made without departing from the scope or spirit of the present disclosure. The above detailed description, therefore, is not to be taken in a limiting sense. While the present disclosure is not so limited, an appreciation of various aspects of the disclosure will be gained through a discussion of the examples provided.

Unless otherwise indicated, all numbers expressing feature sizes, amounts, and physical properties are to be understood as being modified by the term "about," whether or not the term "about" is immediately present. Accordingly, unless indicated to the contrary, the numerical parameters set forth are approximations that can vary depending upon the desired properties sought to be obtained by those skilled in the art utilizing the teachings disclosed herein.

As used herein, the singular forms "a", "an", and "the" encompass implementations having plural referents, unless the content clearly dictates otherwise. As used in this specification and the appended claims, the term "or" is generally employed in its sense including "and/or" unless the content clearly dictates otherwise.

Spatially related terms, including but not limited to, "bottom," "lower", "top", "upper", "beneath", "below", "above", "on top", "on," etc., if used herein, are utilized for ease of description to describe spatial relationships of an element(s) to another. Such spatially related terms encompass different orientations of the device in addition to the particular orientations depicted in the figures and described herein. For example, if a structure depicted in the figures is turned over or flipped over, portions previously described as below or beneath other elements would then be above or over those other elements.

Since many implementations of the invention can be made without departing from the spirit and scope of the invention, the invention resides in the claims hereinafter appended. Furthermore, structural features of the different implementations may be combined in yet another implementation without departing from the recited claims.

What is claimed is:

1. A lab-on-a-chip electrophoresis system comprising:
    a sample device comprising:
        a fluid path comprising a capillary structure having a main branch with an inlet at a first end, the capillary structure also having a first branch terminating at a first outlet and a second branch terminating at a second outlet, both the first outlet and the second outlet at a second end of the fluid path;
        a separation gel within the fluid path; and
        a voltage source configured to provide a voltage differential at the inlet, the first outlet and the second outlet, the voltage source configured to independently control the voltage differential at the first outlet and the second outlet in relation to the inlet; and
    a control device comprising:
        a control fluid path comprising a control capillary structure having an elongate, unbranched structure having a control inlet at a first end and a control outlet at a second end;
        a separation gel within the control fluid path; and
        a control voltage source configured to provide a voltage differential at the control inlet and the control outlet;
    wherein the sample device and the control device are on a lab-on-a-chip.

2. The electrophoresis system of claim 1, wherein the main branch of the sample device terminates where the first branch and the second branch begin.

3. The electrophoresis system of claim 1, wherein the capillary structure of the sample device is longitudinally symmetrical.

4. The electrophoresis system of claim 1, wherein the lab-on-a-chip is an electrode-gridded lab-on-a-chip.

5. The electrophoresis system of claim 1, further comprising a recycle path from the control outlet at the second end of the control capillary structure to the control inlet at the first end of the control capillary structure.

6. The electrophoresis system of claim 1, wherein the fluid path and the control fluid path are on the lab-on-a-chip, wherein the lab-on-a-chip is an electrode-gridded lab-on-a-chip having a plurality of cells, with at least some of the cells of the electrode-gridded lab-on-a-chip operably and independently connected to one of the voltage source and the control voltage source and independently controllable to receive a voltage.

7. The electrophoresis system of claim 6, wherein the fluid path and the control fluid path are non-physically bounded.

8. The electrophoresis system of claim 6, wherein the fluid path and the control fluid path are physically bounded.

9. The electrophoresis system of claim 1, wherein the fluid path and the control fluid path are non-physically bounded.

10. The electrophoresis system of claim 1, wherein the fluid path and the control fluid path are physically bounded.

11. A method comprising:
    providing the lab-on-a-chip electrophoresis system of claim 1;
    migrating a DNA sample through the fluid path from the first end of the fluid path to separate the DNA sample into separated DNA bands based on DNA strand length, and migrating a marked DNA sample through the control fluid path from the first end of the control fluid path to separate the marked DNA sample into separated DNA bands based on DNA strand length;

responsive to applying a positive voltage proximate the first outlet, passing at least one separated DNA band through the first outlet; and responsive to applying a positive voltage proximate the second outlet, passing at least one different separated DNA band through the second outlet.

12. The method of claim 11, wherein providing the fluid path comprises providing the separation gel on the lab-on-a-chip, wherein the lab-on-a-chip is an electrode gridded lab-on-a-chip.

13. The method of claim 11, wherein migrating a DNA sample to separate the DNA sample into separated DNA bands based on DNA strand length and migrating a marked DNA sample to separate the marked DNA sample into separated DNA bands based on DNA strand length are done at the same time.

\* \* \* \* \*